US008908171B2

(12) United States Patent
Makuuchi et al.

(10) Patent No.: US 8,908,171 B2
(45) Date of Patent: Dec. 9, 2014

(54) DEFECT INSPECTION METHOD AND DEFECT INSPECTION DEVICE

(75) Inventors: Masami Makuuchi, Yokohama (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/996,613

(22) PCT Filed: Nov. 25, 2011

(86) PCT No.: PCT/JP2011/006555
§ 371 (c)(1),
(2), (4) Date: Jun. 21, 2013

(87) PCT Pub. No.: WO2012/086128
PCT Pub. Date: Jun. 28, 2012

(65) Prior Publication Data
US 2013/0286387 A1    Oct. 31, 2013

(30) Foreign Application Priority Data
Dec. 22, 2010  (JP) ................. 2010-285284

(51) Int. Cl.
*G01N 21/00* (2006.01)
*G01N 21/95* (2006.01)

(52) U.S. Cl.
CPC ................. *G01N 21/9501* (2013.01)
USPC .......... 356/237.2; 356/237.3; 356/237.4; 356/237.5

(58) Field of Classification Search
CPC .. G01B 11/161; G01B 17/02; G01B 2290/25; G01B 11/026; G01B 11/14; G01N 2291/0258; G01N 2291/02854; G01N 2291/0421; G01N 2291/2636; G01N 29/043; G01N 29/0645; G01N 29/07; G01N 29/2418
See application file for complete search history.

(56) References Cited

U.S. PATENT DOCUMENTS

| 4,376,951 | A | * | 3/1983 | Miyazawa ................. 348/127 |
| 6,621,571 | B1 | * | 9/2003 | Shishido et al. ........... 356/237.5 |
| 2005/0083519 | A1 | * | 4/2005 | Maeda et al. .............. 356/237.2 |
| 2007/0157730 | A1 | * | 7/2007 | Ochiai et al. .................... 73/627 |
| 2008/0015810 | A1 | | 1/2008 | Matsui |

FOREIGN PATENT DOCUMENTS

| JP | A-2-136765 | 5/1990 |
| JP | 2-290534 | 11/1990 |
| JP | 5-332929 | 12/1993 |
| JP | 2000-338048 | 12/2000 |
| JP | 2005-214758 | 8/2005 |
| JP | 2008-8803 | 1/2008 |
| JP | 2008-20374 | 1/2008 |
| JP | A-2008-20271 | 1/2008 |

* cited by examiner

OTHER PUBLICATIONS

Office Action in JP2010-285284, mailed Jun. 17, 2014 (in Japanese, 5 pgs.) [in Japanese], partial English language translation (1 pg.).

*Primary Examiner* — Michael P Stafira
(74) *Attorney, Agent, or Firm* — Antonelli, Terry, Stout & Kraus, LLP.

(57) ABSTRACT

When the intensity of scattering light from a defect on a sample becomes very low according to the diameter of the defect, the dark noise from a sensor device itself accounts which a large proportion of the detected signal outputted from the sensor and thus it is difficult to detect minute defects. Furthermore, since a laser light source is pulsed into oscillation, pulse components from the laser light source are superimposed on the detected signal outputted from the sensor, and therefore it is difficult to detect defects with high accuracy. The present invention is a defect inspection device having irradiation means which producing pulsed operation and irradiating a surface of a sample with a laser beam, detection means which detecting scattering light generated at the surface of the sample in response to the irradiation provided by the irradiation means, and a processing portion which generating a delay signal based on the laser beam emitted by the irradiation means and processing the scattering light detected by the detection means using the delay signal.

10 Claims, 5 Drawing Sheets (a) CONFIGURATION OF CLOCK DETECTION PORTION (b) OPERATION OF CLOCK REPRODUCING CIRCUIT

DEFECT INSPECTION METHOD AND DEFECT INSPECTION DEVICE

TECHNICAL FIELD

The present invention relates to a defect inspection method and defect inspection device.

BACKGROUND ART

In order to maintain and/or improve product yield on a manufacturing line for semiconductor substrates, thin film substrates, or the like, it is necessary to inspect defects existing on the surfaces of semiconductor substrates, thin film substrates, or the like.

To detect minute defects on sample surfaces, a method of detecting defects having dimensions of tens of nm to several μm or more is available, for example. The method consists of irradiating a wafer surface with a focused laser beam and gathering and detecting light scattering from defects.

JP-A-2008-20374 (Patent Literature 1) is available as a background art technique of the present technical field. Disclosed in this publication is "a defect inspection device or tool comprising a light source means emitting a laser in pulsed operation, an irradiation optical system means for controlling the state of polarization of the laser emitted from the light source means and directing the laser at a sample, a detection means for detecting light reflected and scattered from the sample, and a signal processing means for processing a detected signal detected by the detection means and detecting defects on the sample" (refer to the claims).

Defects referred to herein include particles (foreign matter) adhering to wafers, crystal originated particle (COP) defects, and scratches caused by polishing.

CITATION LIST

Patent Literature

Patent Literature 1: JP-A-2008-20374

SUMMARY OF INVENTION

Technical Problem

In the defect inspection device or tool disclosed in Patent Literature 1, the light source means for emitting laser in pulsed oscillation and the irradiation optical system means for controlling the state of polarization of the laser emitted from the light source means and directing the laser at a sample are disclosed. Where the intensity of light scattered from a defect on a sample is quite small depending on the diameter of the defect, for example, dark noises of the sensor device itself account for a large proportion of the detected signal outputted from the sensor. This makes it difficult to detect microscopic defects. Furthermore, the laser light source is generating light in pulsed operation and it follows that pulse components of the laser light source are also superimposed on the detected signal outputted from the sensor. This makes it difficult to detect defects at high accuracy.

Accordingly, the present invention offers a defect inspection method and inspection device for reducing the effects of dark noise of a sensor device and of pulsed oscillation of a laser light source.

Solution to Problem

To solve the foregoing problem, configurations set forth in the claims are adopted, for example.

The present application includes plural means that solve the foregoing problem. One example is a defect inspection device having irradiation means for providing pulsed operation and irradiating a surface of a sample with a laser beam, detection means for detecting scattering light generated at the surface of the sample by the irradiation provided by the irradiation means, and processing portion for generating a delay signal based on the laser beam directed by the irradiation means and processing the scattering light detected by the detection means by the use of the delay signal.

Advantageous Effects of Invention

According to the present invention, microscopic defects can be detected by reducing the effects of dark noise of a sensor device and of pulsed operation of a laser light source.

Problems, configurations, and advantageous effects other than the foregoing will become apparent from the description of the following embodiments.

DESCRIPTION OF EMBODIMENTS

Embodiments are hereinafter described with reference to the drawings.

Embodiment 1

In the present embodiment, an example of defect inspection device for reducing the effects of dark noise of a sensor device and of pulsed oscillation of a laser light source is described.

Figure 1:
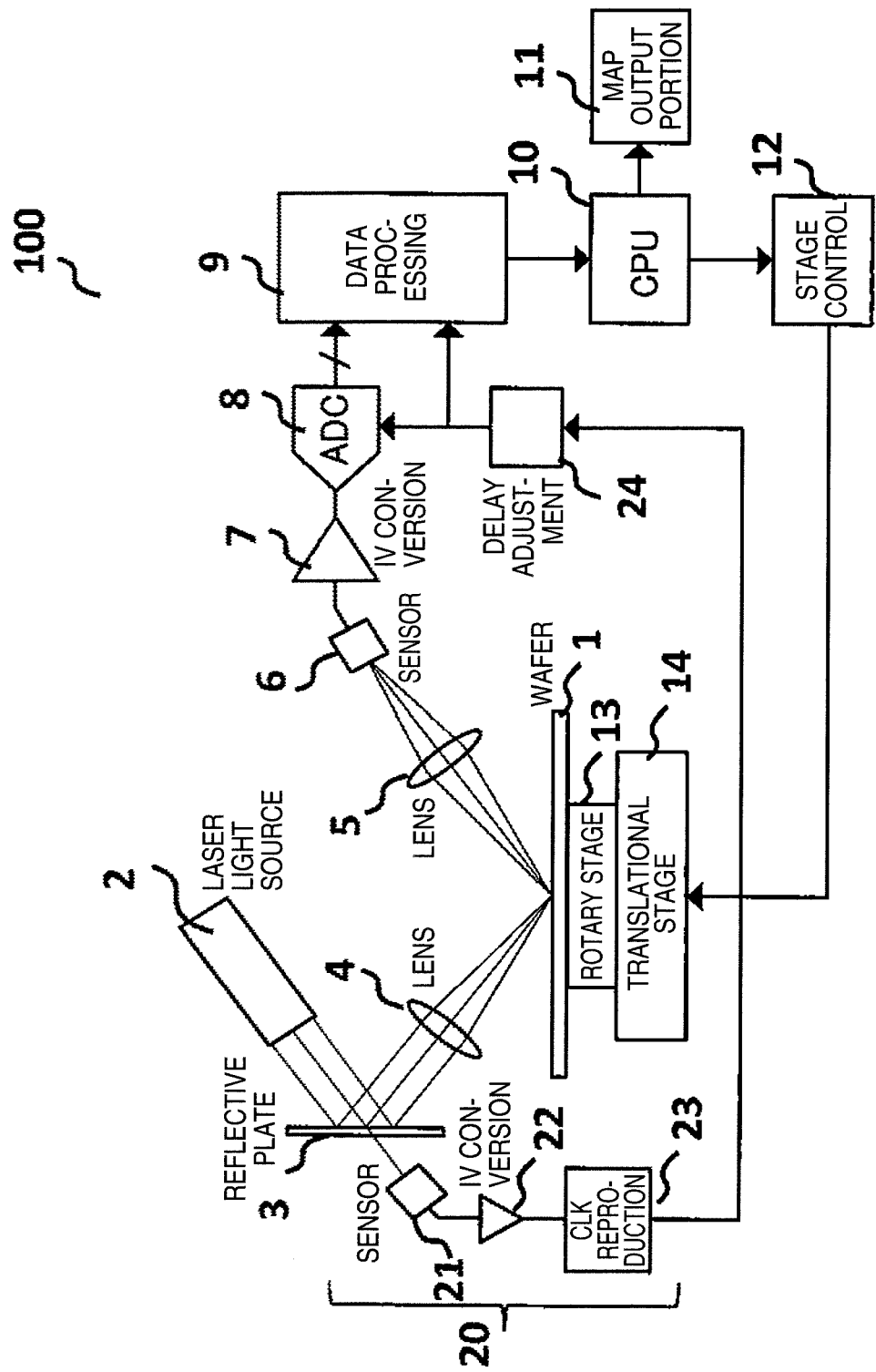
FIG. 1 is an example of a block diagram of a defect inspection device according to a first embodiment.

FIG. 1 is an example of block diagram of a defect inspection device of the present embodiment.

A defect inspection device 100 is configured having a laser light source 2, a reflective plate 3, lenses 4, 5, a sensor 6, an IV converter circuit 7, an A/D converter circuit 8, a data processing portion 9, a CPU 10, a map output portion 11, a stage control portion 12, a rotary stage 13, a translational stage 14, a clock detection portion 20, and a delay control portion 24.

The stage portion constitutes the rotary stage 13 and the translational stage 14 on which a sample such as a semiconductor wafer 1 is mounted.

An irradiation optical system is configured having the laser light source 2 emitting a laser beam (laser light) in pulsed oscillation, the reflective plate 3 for reflecting the laser beam emitted from the laser light source 2 in a direction towards the wafer 1, and the lens 4 for gathering and focusing the laser beam (laser output) 51 reflected by the reflective plate 3.

A detection optical system is configured having the lens 5 for gathering and focusing light scattered at the surface of the wafer 1 irradiated by the irradiation optical system and the sensor 6 for detecting the scattering light gathered and focused by the lens 5 and for providing a sensor output 52.

A processing portion is configured having the clock detection portion 20 for detecting the laser beam emitted from the laser light source 2 and generating a clock signal synchronized with the laser light source 2, the delay control portion 24 for finding an optimum set value of sampling timing based on the clock signal generated by the clock detection portion 20, the IV converter circuit 7 for subjecting the sensor output 52 to IV conversion and providing an output, the A/D converter circuit 8 for sampling the output from the IV converter circuit 7 based on the delay signal from the delay control portion 24 and providing an ADC output 53, the data processing portion 9 for data processing the PC output 53 and extracting defects, the CPU 10 for sending the results of the data processing performed by the data processing portion 9, the map output portion 11 for outputting maps indicative of the results of the data processing delivered from the CPU 10, and the stage control portion 12 for controlling the motion of the stage portion based on the results of the data processing delivered from the CPU 10.

Figure 2:
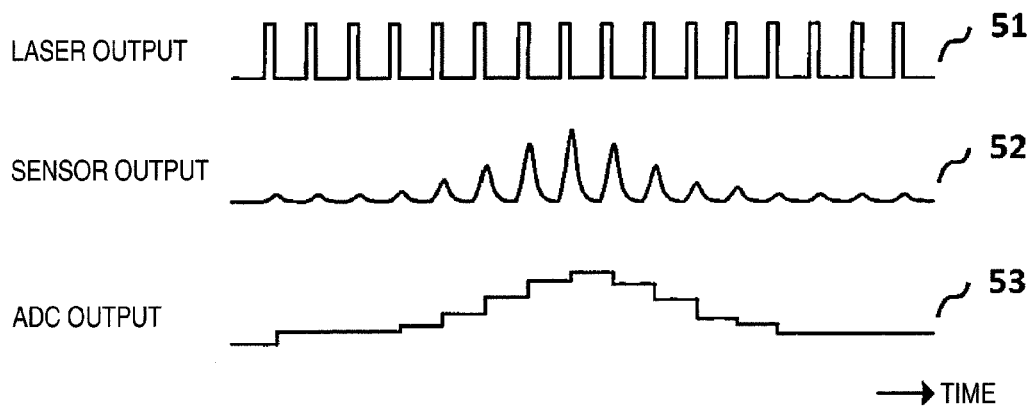
FIG. 2 is an example of operation of the defect inspection device for detection.

FIG. 2 is an example of operation for detecting the laser output 51, sensor output 52, and ADC output 53 in the defect inspection device 100.

The laser beam directed at the surface of the wafer 1 via the lens 4 of the irradiation optical system is referred to as the laser output 51. The signal delivered from the sensor 6 of the detection optical system is referred to as the sensor output 52. The signal converted and delivered by the A/D converter circuit 8 is referred to as the ADC output 53.

At this time, the laser output 51 is in pulsed oscillation. The sensor output signal 52 from the sensor 6 due to the scattering light from defects is also a pulsed signal. Accordingly, in the sensor output signal 52, the signal is effective only at the instant when laser light is delivered from the laser light source 2. The signal is ineffective during the period in which no laser light is delivered from the laser light source 2, and dark noise is generated from the sensor 6 itself.

During inspection, the whole surface of the wafer 1 is irradiated by moving the rotary stage 13 and translational stage 14 on which the wafer 1 is mounted. That is, under control from the CPU 10, the stage control portion 12 rotates the wafer 1 through the rotary stage 13 and linearly moves the wafer 1 through the translational stage 14. Consequently, the laser light incident on the wafer 1 draws a helical trajectory over the whole surface of the wafer 1. Thus, the whole surface of the wafer 1 can be inspected.

When there exist defects on the wafer 1, scattering light is generated at the surface of the wafer 1 by being irradiated with the laser light 51. The scattering light is detected with the sensor 6 via the lens 5. The detected signal (sensor output 52) delivered from the sensor 6 is sampled by the A/D converter circuit 8 via the IV converter circuit 7.

Figure 3:
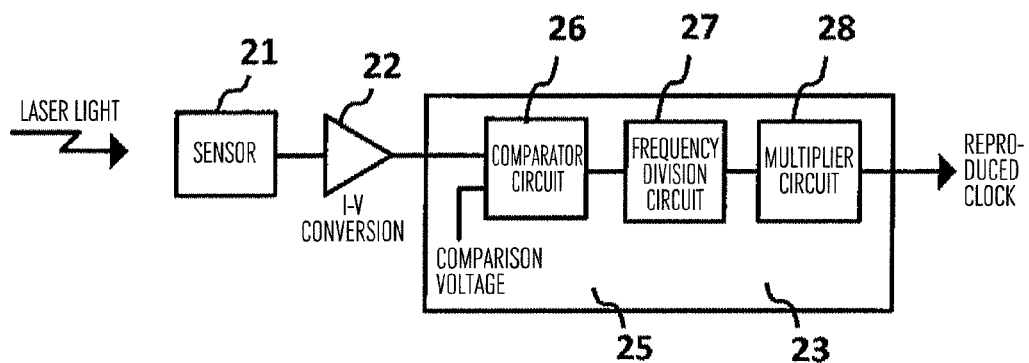
FIG. 3 is a block diagram of a clock detection circuit and an example of operation.
Figure 3:
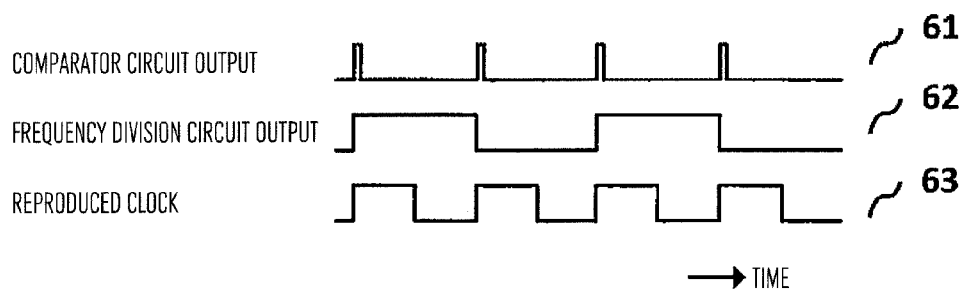

FIG. 3 is an example of block diagram of the clock detection portion 20 and operation. The clock detection portion 20 has a sensor 21 for detecting the laser beam emitted from the laser light source 2, an IV converter circuit 22 for subjecting the laser beam detected by the sensor 21 to IV conversion, and a clock regeneration circuit 23 (including a comparator circuit 26, a frequency division circuit 27, and a multiplier circuit 28) for generating a clock signal synchronized with the laser light source 2 based on the signal converted by the IV converter circuit 22. In the clock detection portion 20, a clock signal synchronized with the laser light source 2 is generated based on the laser light transmitted through the reflective plate 3 after exiting from the laser light source 2.

The clock signal generated by the clock detection portion 20 is adjusted in delay via the delay adjusting portion (delay control portion) 24. A signal delivered by the IV converter circuit 7 based on this is sampled by the A/D converter circuit 8 to thereby obtain the ADC output 53.

The incidence of the laser light generates a signal via the sensor 21 and the IV converter circuit 22. The signal is compared with a comparison voltage 25 by the comparator circuit 26 and becomes a signal on pulses indicated by a comparison circuit output 61. Then, the signal is frequency divided by the frequency division circuit 27 into a frequency division circuit output 62 that is half in frequency of the laser oscillation. Furthermore, a clock signal with a double frequency of the frequency division output 62 is produced via the multiplier circuit 28. As a result, reproduced clock 63 becomes a clock signal that has the same frequency as the comparator circuit output 61, i.e., laser oscillation, and a duty ratio of about 50%. Using the reproduced clock 63, the delay adjusting portion 24, A/D converter circuit 8, and data processing portion 9 in later stages are operated.

For the sake of illustration, the frequency division circuit 27 is set to one half, and the multiplier circuit 28 is set to twice. Obviously, the invention is not restricted to this ratio if equivalent effects are obtained by a desired operation of the A/D converter circuit 8 based on the laser oscillation. The frequency division circuit 27 and multiplier circuit 28 included in the clock generating circuit 23 may be integrated into a PLL circuit and it is used. In addition, a clock signal having a duty ratio close to about 50% can be generated using a delay means.

Figure 4:
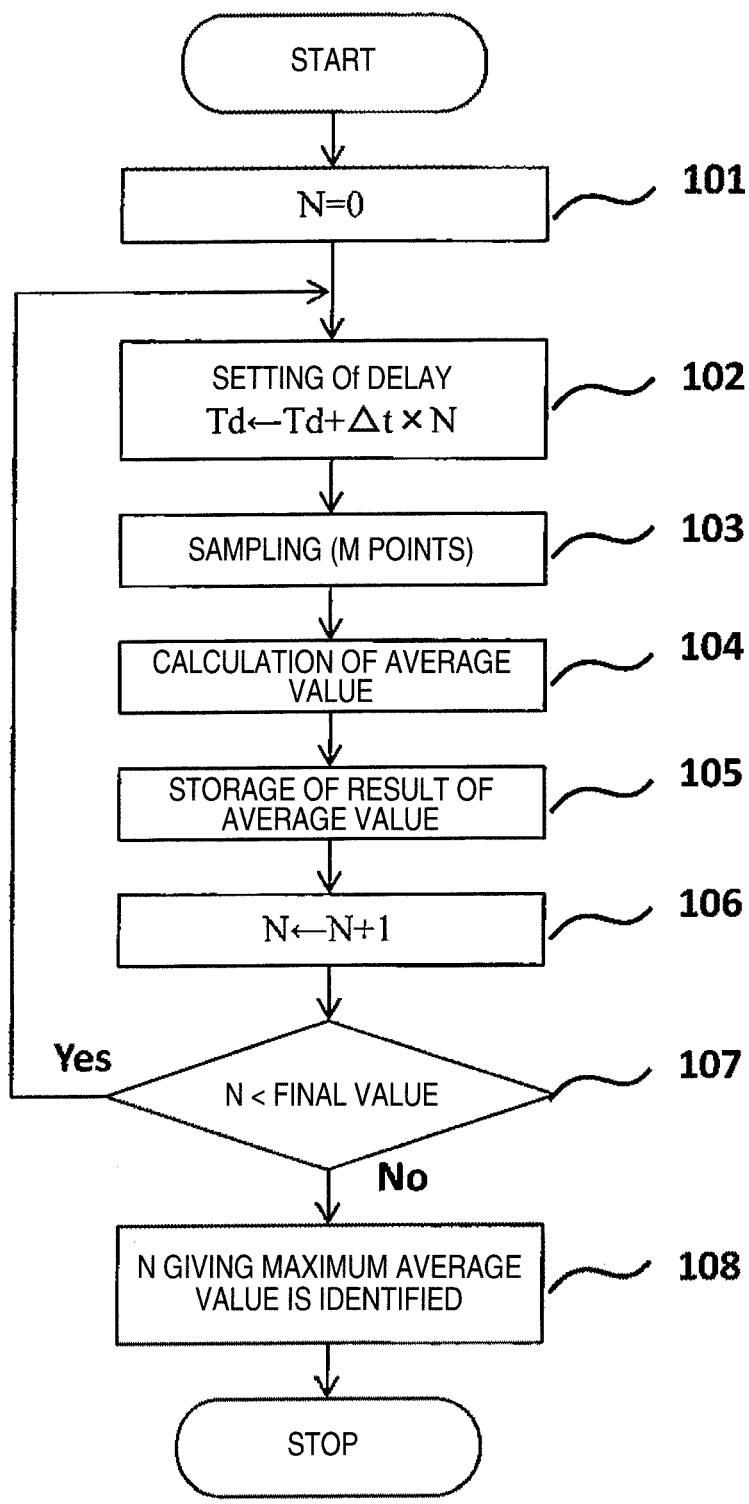
FIG. 4 is an example of flowchart for finding an optimum set value for a delay control portion.

FIG. 4 is an example of flowchart for finding an optimum set value of the sampling timing in the delay control portion 24.

In the defect inspection device 100, the detected signal is effective only at the instant when laser light is delivered from the laser light source 2 and, therefore, when the detected signal is sampled by the A/D converter circuit 8 based on the reproduced clock, it is necessary to optimally set the sampling timing.

The optimal set value of the sampling timing in the delay control portion 24 is carried out prior to a defect inspection as a calibration operation of the defect inspection device 100 such as irradiation of the wafer 1 with a laser beam or detection of scattering light.

In the flow of execution, a variable N is first set to 0 (step 101). The set delay value of the sampling timing in the delay control portion is set according to the variable N (step 102). Then, M data points are sampled by the D converter circuit 8 (step 103), and the average value of the sampled data is calculated (step 104). The result of calculation of the average value is stored in a memory such that the variable N is made to correspond to an address (step 105). The variable N is increased (step 106). Where the variable N is equal to or less than a preset final value (step 107), the steps 102 to 106 are repeated. Where the variable N exceeds the final value, the results of calculations of the average value stored in the memory are compared and N giving a maximum average value is identified (step 108). Since the sensor 6 output at the moment when laser light is produced is greater than the dark noise of the sensor 6 itself, it follows that the set delay value of the reproduced clock corresponds to N giving the maximum average value.

Figure 5:
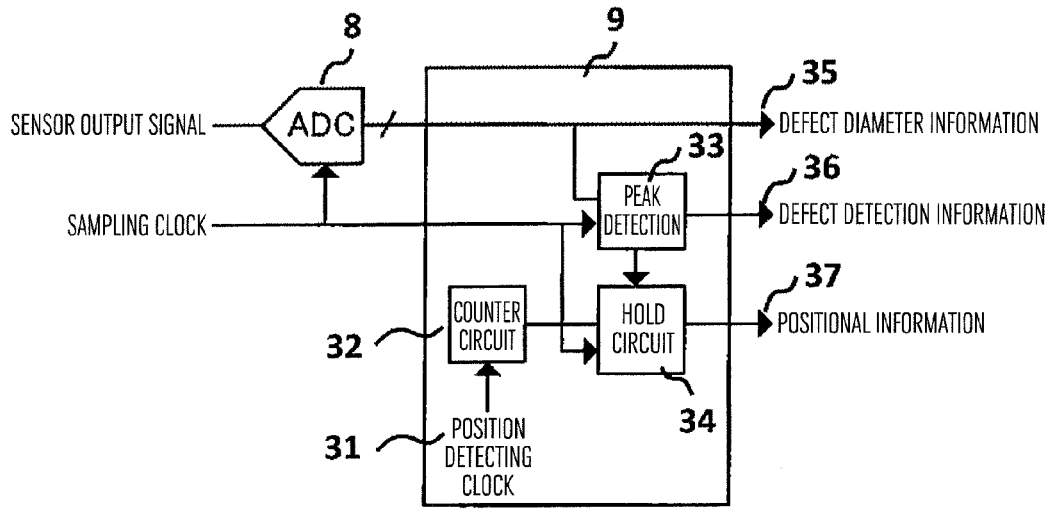
FIG. 5 is an example of block diagram of a data processing portion.

FIG. 5 is an example of block diagram of the data processing portion 9 in the defect inspection device 100.

The data processing portion 9 is configured having a peak detection circuit 33, a counter circuit 32 operated by a position detection clock 31, and a hold circuit 34.

The position detecting clock 31 is a clock signal oscillating in synchronism with the operation of the rotary stage 13 for rotating the wafer 1 and of the translational stage 14 for translating the wafer 1, as well as a signal associated with the position of a beam incident on the wafer 1. The signal is generated inside the defect detection device 100, e.g., by the stage control portion 12 (not shown).

The peak detection circuit 33 detects the peak value of sampled data, based on the output data from the A/D converter circuit 8 and the optimal set value data of the sampling timing determined in the delay control portion 24, and outputs defect detection information 36 based on it. At the same time, the hold circuit 34 maintains the output from the counter circuit 32 and outputs positional information 37, based on the results of transmission from the peak detection circuit 33, on the signal from the counter circuit 32, and on the optimal set value data about the sampling timing determined in the delay control portion 24. Also, the output data from the A/D converter circuit 8 becomes defect diameter information 35. The CPU 10 in the later stage outputs defect detection results as a monitor view via the map output portion 12, based on the aforementioned defect detection information 36, defect diameter information 35, and positional information 37.

Figure 6:
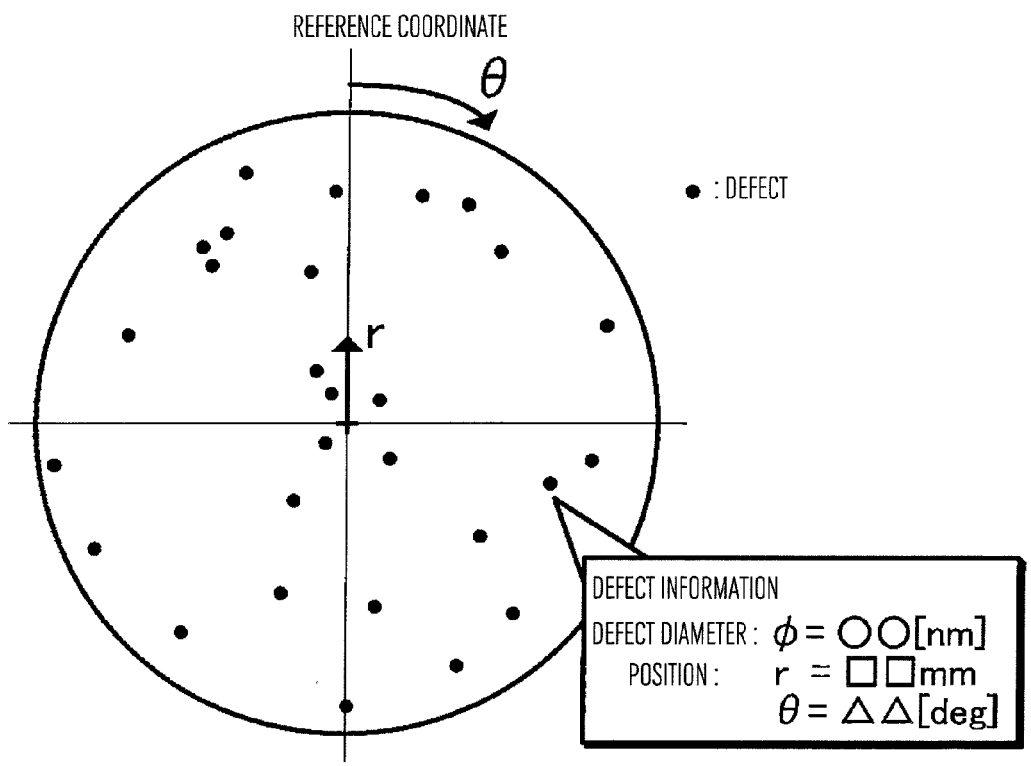
FIG. 6 is an example of monitor view showing the results of detection of defects.

FIG. 6 is an example of monitor view indicating the results of defect detection.

This indicates a position where a defect is detected on reference coordinates on the surface of the wafer 1 defined in terms of r and θ. As described in FIG. 5, the defect diameter information 35, the defect detection information 36, and the positional information 37 are obtained and so defect diameters and positions are displayed as defect information about extracted defects on the monitor view of FIG. 6.

Embodiment 2

In the present embodiment, an example of defect inspection device which not only reduces the effects of dark noise of a sensor device and pulsed oscillation of a laser light source but also achieves lower cost by simplifying the instrumental configuration is described.

Figure 7:
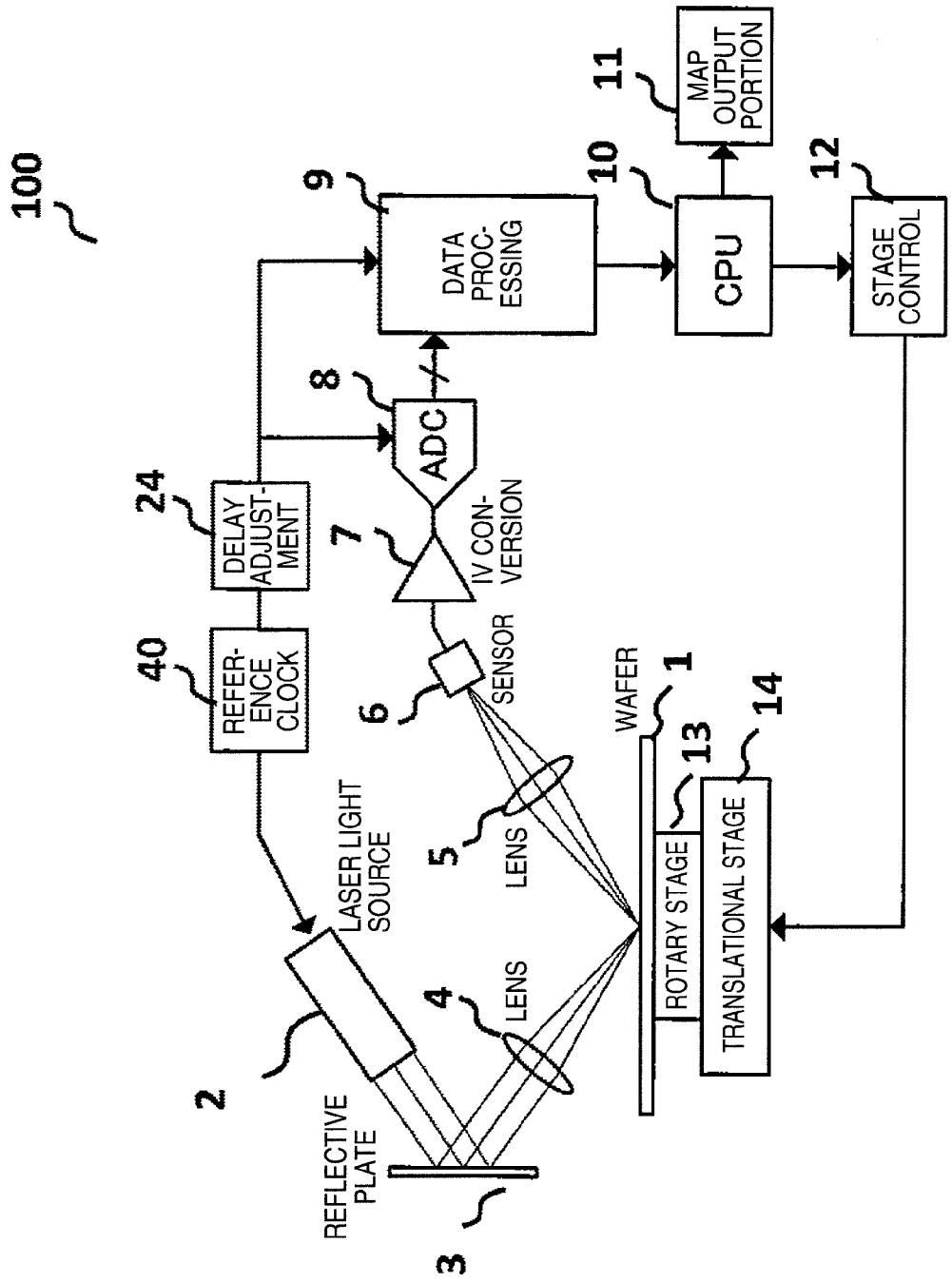
FIG. 7 is an example of block diagram of a defect inspection device according to a second embodiment.

FIG. 7 is an example of block diagram of a defect inspection device of the present embodiment. To avoid complicating the explanation, a description of constituent elements indicated by the same reference numerals as in Embodiment 1 is omitted.

A defect inspection device 100 shown in FIG. 7 is characterized in that it has a reference clock generating circuit 40. The laser light source 2 pulse oscillates based on the clock signal delivered from the reference clock generating circuit 40. A detection operation is performed in the A/D converter circuit 8 and data processing portion 9 via the delay adjustment circuit 34.

In comparing the defect inspection device associated with the present embodiment with the defect inspection device 100 shown in FIG. 1, both laser oscillation and detection operation can be achieved with a common reference clock without using the clock detection portion 20. The effects of the dark noise of the sensor device and the pulsed oscillation of the laser light source are reduced. In addition, a stable detection operation is achieved without depending on the laser output intensity. Also, lower cost can be achieved while suppressing the constituent elements of the instrument.

It is to be understood that the present invention is not restricted to the above embodiments but rather embraces various modifications. For instance, the above embodiments have been described in detail such that the present invention is explained in an easily understandable manner. The invention is not limited to those having all the configurations described. Some of the configurations of some embodiment may be replaced by configurations of other embodiments. In addition, configurations of other embodiments may be added to configurations of one embodiment. Further, with respect to some configurations of each embodiment, addition, erasure, and replacement of other configurations may be made.

Furthermore, the above-described configurations, functions, processing portions, processing means, and so on may be realized in hardware by designing some or all of them, for example, using an integrated circuit. Additionally, the above-described configurations, functions, and so on may be realized by software such that a CPU interprets programs that achieve respective functions.

While the aspects of the present invention have been described thus far using its embodiments, the defect inspection device can sample a sensor output in synchronism with pulsed emission of a laser light source at optimum timing by applying the present invention. Dark noise detection of a sensor device contained in the sensor output signal during non-emission can be removed. Since the sampling is done at the same frequency as the pulsed emission of the laser light source, an inexpensive A/D converter of high-bit resolution can be applied without using an expensive high-speed A/D converter with low bit resolution. The detection accuracy of the defect inspection device can be enhanced. Also, lower cost can be accomplished.

Reference Signs List

1: wafer; 2: laser light source; 3: reflective plate; 4, 5: lenses; 6: sensor; 7: IV converter circuit; 8: converter circuit; 9: data processing portion; 10: CPU; 11: map output portion; 12: stage control portion; 13: rotary stage; 14: translational stage; 20: clock detection portion; 21: sensor; 22: IV converter circuit; 23: clock regeneration circuit; 24: delay control portion; 25: comparison voltage; 26: comparator circuit; 27: frequency division circuit; 28: multiplier circuit; 31: position detection clock; 32: counter circuit; 33: peak detection circuit; 34: hold circuit; 35: defect diameter information; 36: defect detection information; 37: positional information; 40: reference clock generating circuit; 100: defect inspection device

The invention claimed is:

1. A defect inspection device comprising:
   an irradiation means which pulse oscillates and irradiates a surface of a sample with a laser beam;
   a detection means which detects scattering light generated at the surface of the sample by the irradiation provided by the irradiation means; and
   a processing portion comprising a delay control portion which generates a delay signal based on the laser beam emitted by the irradiation means and an A/D converter circuit which samples the scattering light detected by the detection means using the delay signal generated by the delay control portion,
   wherein the delay control portion is configured so that an optimum value of timing at which the scattering light is sampled is determined based on a timing at which the laser beam is emitted by the irradiation means.

2. The defect inspection device according to claim 1, wherein the delay control portion determines an optimum value of timing at which the scattering light is sampled, by setting a set delay value of timing at which the scattering light is sampled according to a variable N (N≥0),
   sampling M (natural number) data points at every variable N in the A/D converter circuit based on the set delay value,
   calculating an average value of the sampled data at every variable N, and identifying N giving a maximum value of the calculated average value.

3. The defect inspection device according to claim 1,
wherein the processing portion includes a clock detection portion which generates a clock signal synchronized with the irradiation provided by the irradiation means based on the laser beam, and
wherein the delay control portion is configured to adjust the clock signal in delay and generates a delay signal.

4. A defect inspection method comprising the steps of:
pulse oscillating and irradiating a surface of a sample with a laser beam;
detecting scattering light generated at the surface of the sample by the irradiating step;
delay controlling by generating a delay signal based on the laser beam emitted by the irradiating step; and
A/D converting to sample the scattering light detected in the detecting step using the delay signal generated in the delay controlling step; and
wherein delay controlling step includes determining an optimum value of timing at which the scattering light is sampled based on the laser beam emitted in the irradiation step.

5. The defect inspection method according to claim 4, wherein during the step of controlling delay, an optimum value of timing at which the scattering light is sampled is determined by setting a delay value of timing at which the laser beam is sampled according to a variable N(N≥0),
sampling M (natural number) data points at every variable N in the AID converter circuit based on the set delay value,
calculating an average value of the sampled data at ever variable N and
identifying N giving a maximum value of the calculated average value.

6. The defect inspection method according to claim 4,
wherein the processing step includes generating a clock signal synchronized with the irradiation provided in the irradiating step based on the laser beam, and
wherein during the step of controlling delay, the clock signal is adjusted in delay and the delay signal is generated.

7. A defect inspection device comprising:
a reference clock generating circuit which outputs a given clock signal;
an irradiating means which pulse oscillates and irradiates a surface of a sample with a laser beam based on the clock signal outputted by the reference clock generating circuit;
a detection means which detects scattering light generated at the surface of the sample by the irradiation provided by the irradiating means;
a processing means which processes the scattering light detected by the detection means based on the clock signal outputted by the reference clock generating circuit,
a delay control means which generates a delay signal based on the clock signal outputted by the reference clock generating circuit; and
an A/D converter circuit which samples the scattering light detected by the detection means using the delay signal generated by the delay control means;
wherein the delay control means is configured to determine an optimum value of timing at which the scattering light is sampled based on the clock signal outputted by the reference clock generating circuit.

8. The defect inspection device according to claim 1,
wherein the delay control portion is configured to determine the optimum value of timing in a manner to decrease effects of dark noise generated by the detection means during detection of the scattering light.

9. The defect inspection device according to claim 4,
wherein the delay controlling step includes determining the optimum value of timing in a manner to decrease effects of dark noise of a detector used in the detecting step.

10. The defect inspection device according to claim 7,
wherein the delay control portion is configured to determine the optimum value of timing in a manner to decrease effects of dark noise generated by the detection means during detection of the scattering light.

* * * * *